(12) United States Patent
Nakao et al.

(10) Patent No.: US 8,997,787 B2
(45) Date of Patent: Apr. 7, 2015

(54) FLUID HANDLING APPARATUS AND FLUID HANDLING SYSTEM

(75) Inventors: Tomoki Nakao, Saitama (JP); Koichi Ono, Saitama (JP)

(73) Assignee: Enplas Corporation, Saitama (JP)

( * ) Notice: Subject to any disclaimer, the term of this patent is extended or adjusted under 35 U.S.C. 154(b) by 416 days.

(21) Appl. No.: 13/438,261

(22) Filed: Apr. 3, 2012

(65) Prior Publication Data
US 2012/0247577 A1 Oct. 4, 2012

(30) Foreign Application Priority Data

Apr. 4, 2011 (JP) ................................ 2011-082819

(51) Int. Cl.
*F15C 1/06* (2006.01)
*G01N 27/447* (2006.01)
*B01L 3/00* (2006.01)

(52) U.S. Cl.
CPC ..... *G01N 27/44791* (2013.01); *B01L 3/502707* (2013.01)

(58) Field of Classification Search
USPC ............................. 137/341, 827, 833; 422/503
See application file for complete search history.

(56) References Cited

U.S. PATENT DOCUMENTS

| 6,939,451 | B2 | 9/2005 | Zhao et al. | |
| 7,159,618 | B2 * | 1/2007 | Broyer et al. | 137/828 |
| 2002/0110492 | A1 * | 8/2002 | Handique | 422/100 |
| 2006/0216203 | A1 * | 9/2006 | Fuller et al. | 422/82.01 |

FOREIGN PATENT DOCUMENTS

JP 2007-248281 A 9/2007

OTHER PUBLICATIONS

Machine Translation of JP 2007-248281.

* cited by examiner

*Primary Examiner* — Kevin Murphy
(74) *Attorney, Agent, or Firm* — Brundidge & Stanger, P.C.

(57) ABSTRACT

Bottomed first regions 23a' and 23b', and second regions 24a' and 24b' are formed by joining film 14 to undersurface 21 of chip body 12 of a micro-channel chip. Third regions 25a' and 25b' are formed between first regions 23a' and 23b', and second regions 24a' and 24b' so as to be located on carbon inks 16a and 16b. The width of third regions 25a' and 25b' is formed so as to be greater than the width of carbon inks 16a and 16b.

2 Claims, 10 Drawing Sheets

FLUID HANDLING APPARATUS AND FLUID HANDLING SYSTEM

CROSS REFERENCE TO RELATED APPLICATIONS

This application is entitled and claims the benefit of Japanese Patent Application No. 2011-082819, filed on Apr. 4, 2011, the disclosure of which including the specification, drawings and abstract is incorporated herein by reference in its entirety.

TECHNICAL FIELD

The present invention relates to a fluid handling apparatus and a fluid handling system provided therewith used for an analysis, processing or the like of a fluid sample.

BACKGROUND ART

In recent years, micro-analytical systems are used to carry out an inspection/analysis of trace substances such as proteins, nucleic acids (e.g., DNA) accurately and at high speed in the scientific field such as biochemistry and analytical chemistry or medical field.

As an example of the micro-analytical system, there is a system which fills a channel formed on a micro-channel chip with a buffer solution, injects a sample from an injection port connected to the channel, applies a voltage to both ends of the channel and electrophoreses the sample to conduct an analysis.

The micro-channel chip is manufactured by joining a film (thin film) or thin plate to the chip body in which the channel is formed. A reservoir into which a liquid is injected is formed at both ends of the channel and a electrode is formed in each reservoir. As an example of an electrode forming method, a method whereby an electrode pattern is printed on a film or thin plate with a carbon ink is known (see Patent Reference). One end of the electrode pattern is formed so as to be located inside the reservoir and the other end is formed so as to be located outside the reservoir. The micro-channel chip is configured such that the electrode of the electrophoresis apparatus is made to contact the other end of the electrode pattern and a voltage can be applied to the liquid sample without contacting the liquid sample injected into the reservoir.

Patent Reference: U.S. Pat. No. 6,939,451

According to the above electrode forming method, the peripheral part of the carbon ink of the film or thin plate may remain unbonded (insufficiently laminated) to the chip body depending on the thickness of the carbon ink and the liquid may leak.

However, the background art adopts no measures for this liquid leakage, and the liquid leakage may cause contamination of the electrophoresis apparatus (electrode).

It is an object of the present invention to provide a fluid handling apparatus and a fluid handling system capable of preventing a liquid from leaking from the fluid handling apparatus such as a micro-channel chip and preventing contamination of an external environment.

SUMMARY OF THE INVENTION

In order to attain the above object, a fluid handling apparatus of the present invention includes a substrate member, a cover member joined to one surface of the substrate member, and a transfer function section for transferring electricity or heat, the transfer function section formed on the cover member in a laminar shape so as to cover part of a surface of the cover member, the surface joined to the substrate member, wherein a depression or through hole constituting a first region is formed in the one surface of the substrate member at a portion corresponding to one end of the transfer function section, an opening of the depression or through hole on the one surface side is closed by the cover member, a second region communicating with an outside is formed at a portion corresponding to the other end of the transfer function section, the transfer function section electrically or thermally connects the first region and the second region, a groove constituting a third region is formed on the one surface of the substrate member so as to extend over edges of the transfer function section extending between the first region and the second region, and an opening of the groove is closed by the cover member.

A fluid handling system according to the present invention includes the above fluid handling apparatus.

The present invention forms a groove in a substrate member and can stop a liquid, leaked along a gap between the substrate member and the cover member produced by a thickness of a layered transfer function section, with the groove or can store the liquid in the groove, and can thereby prevent the liquid from leaking out and prevent contamination of an external environment.

DETAILED DESCRIPTION OF PREFERRED EMBODIMENTS

Hereinafter, an embodiment of the present invention will be described in detail with reference to the accompanying drawings. The following description is given using a micro-channel chip as a typical example of a fluid handling apparatus.

[Configuration of Micro-Channel Chip]

Figure 1A:
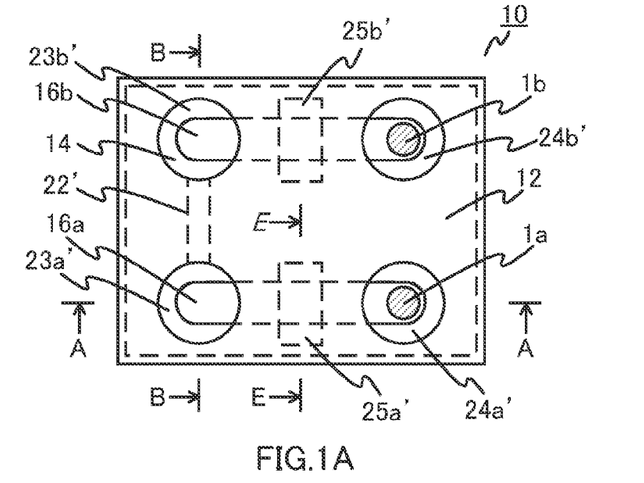
FIG. 1A to FIG. 1D are diagrams illustrating the shape of a micro-channel chip according to an embodiment of the present invention.
Figure 1B:
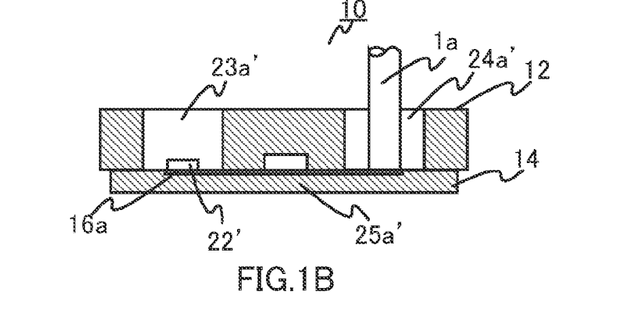
Figure 1C:
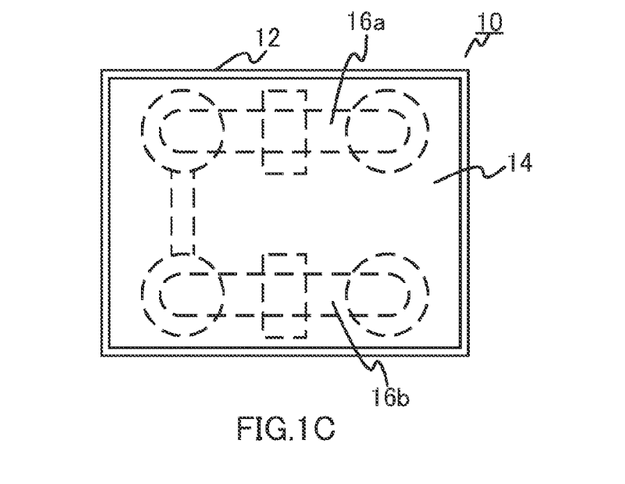
Figure 1D:
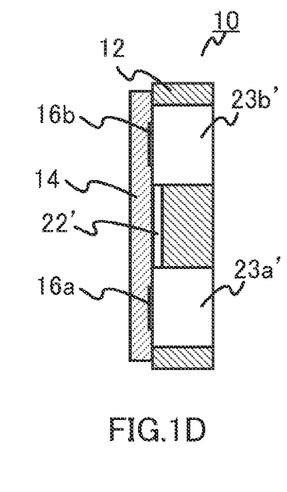

FIG. 1A to FIG. 1D are schematic views illustrating the shape of a micro-channel chip as a fluid handling apparatus according to the present embodiment. FIG. 1A is a plan view, FIG. 1B is a front cross-sectional view along line A-A, FIG. 1C is a bottom view and FIG. 1D is a left side cross-sectional view along line B-B. FIG. 1A and FIG. 1B also show electrode rods $1a$ and $1b$ together.

As shown in FIG. 1A to FIG. 1D, micro-channel chip 10 is constructed of a transparent substantially rectangular flat chip body (substrate member) 12, film (thin film which constitutes a cover member) 14 and carbon inks (electrodes as transfer function sections) $16a$ and $16b$.

The thickness of chip body 12 is approximately 1 mm, the thickness of film 14 is approximately 100 μm and the thickness of carbon inks $16a$ and $16b$ is approximately 10 μm.

Chip body 12 and film 14 are formed of a resin material such as polyethylene terephthalate, polycarbonate, polymethylmethacrylate, vinyl chloride, polypropylene, polyether or polyethylene. Different materials may also be used for chip body 12 and film 14.

Carbon inks $16a$ and $16b$ are printed on film 14. Film 14 is bonded to chip body 12 by adhesion using an organic adhesive or thermo-compression bonding.

Figure 2A:
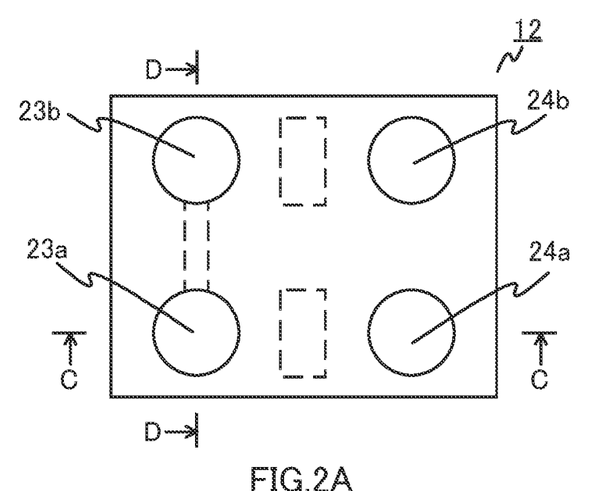
FIG. 2A to FIG. 2D are diagrams illustrating the shape of the chip body of the micro-channel chip shown in FIG. 1A to FIG. 1D.
Figure 2B:
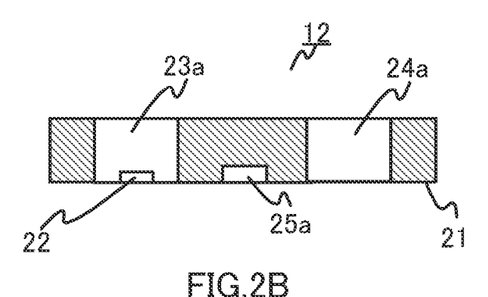
Figure 2C:
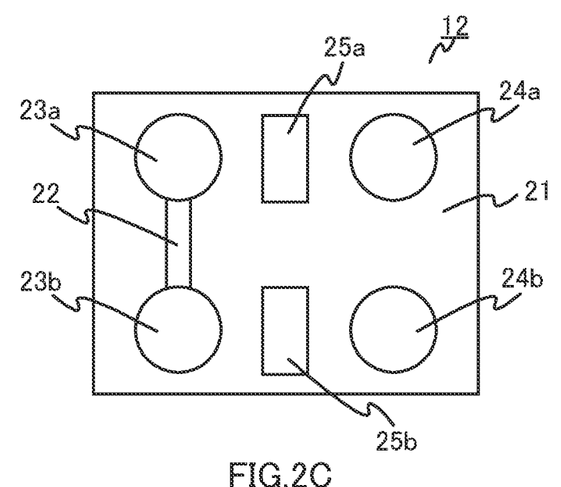
Figure 2D:
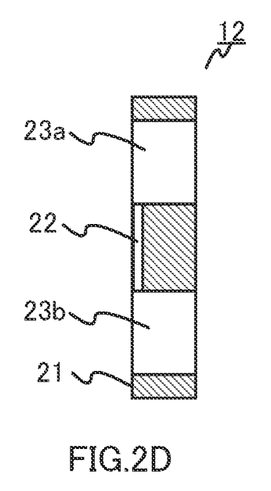

FIG. 2A to FIG. 2D are schematic views illustrating the shape of chip body 12. FIG. 2A is a plan view, FIG. 2B is a front cross-sectional view along line C-C, FIG. 2C is a bottom view, and FIG. 2D is a left side cross-sectional view along line D-D.

Elongated micro-groove 22 is formed on undersurface 21 of chip body 12, which is a surface facing film 14. Micro-groove 22 has a substantially rectangular cross section having a length (width and depth) per side of on the order of several tens of μm. In a condition in which chip body 12 and film 14 are bonded together, channel $22'$ is formed by closing the opening of micro-groove 22 with film 14.

Through holes $23a$ and $23b$ which are open outward, having a quasi-circular cross section are formed at both ends of micro-groove 22 of chip body 12. The diameter of through holes $23a$ and $23b$ is several 100 μm to several mm. In a condition in which chip body 12 and film 14 are bonded together, bottomed first regions $23a'$ and $23b'$ having functions as an injection port and an exhaust port of a buffer solution and a sample are formed by closing openings of through holes $23a$ and $23b$ with film 14.

Through holes $24a$ and $24b$ having a substantially circular cross section are formed on chip body 12. The diameter of through holes $24a$ and $24b$ is several 100 μm to several mm. In a condition in which chip body 12 and film 14 are bonded together, bottomed second regions $24a'$ and $24b'$ having a function of insertion ports of electrode rods $1a$ and $1b$ are formed by closing openings of through holes $24a$ and $24b$ with film 14.

Groove $25a$ is formed at a position between through hole $23a$ and through hole $24a$ on undersurface 21 of chip body 12. Furthermore, groove $25b$ is formed at a position between through hole $23b$ and through hole $24b$ on undersurface 21 of chip body 12. In a condition in which chip body 12 and film 14 are bonded together, third regions $25a'$ and $25b'$ are formed by closing openings of grooves $25a$ and $25b$ with film 14. Third regions $25a'$ and $25b'$ are located on carbon inks $16a$ and $16b$. The width of third regions $25a'$ and $25b'$ is formed so as to be greater than the width of carbon inks $16a$ and $16b$ (see FIG. 4). Third regions $25a'$ and $25b'$ have a function of stopping or storing a liquid leaked from first regions $23a'$ and $23b'$ through unbonded portions (unexpected channels) generated by the thickness of carbon inks $16a$ and $16b$. Details of the function of third regions $25a'$ and $25b'$ will be described later.

Figure 3A:
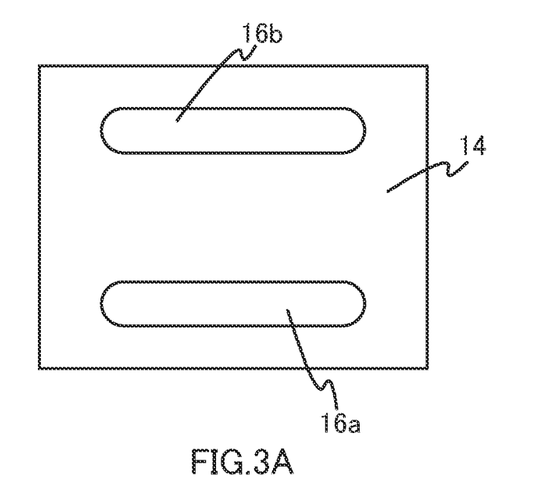
FIG. 3A to FIG. 3C are diagrams illustrating the shape of a film after carbon ink printing of the micro-channel chip shown in FIG. 1A to FIG. 1D.
Figure 3B:
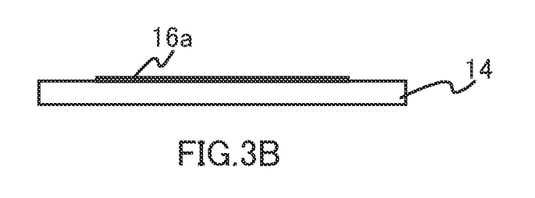
Figure 3C:
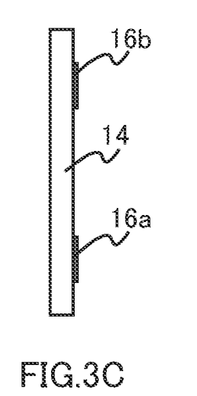

FIG. 3A to FIG. 3C are schematic views illustrating the shape of film 14 after printing carbon inks $16a$ and $16b$. FIG. 3A is a plan view, FIG. 3B is a front view and FIG. 3C is a left side view.

Film 14 with carbon inks $16a$ and $16b$ printed thereon is bonded to undersurface 21 of chip body 12 through adhesion using a transparent organic adhesive or thermo-compression bonding or the like so as to cover at least micro-groove 22, through holes $23a$, $23b$, $24a$ and $24b$ and grooves $25a$ and $25b$.

When film 14 is bonded to chip body 12, both ends of carbon ink $16a$ are located inside first region $23a'$ and inside second region $24a'$ and both ends of carbon ink $16b$ are located inside first region $23b'$ and inside second region $24b'$. Carbon inks $16a$ and $16b$ are provided with conductivity and have functions as electrodes.

[Electrophoresis by Micro-Channel Chip]

First, a buffer solution is injected into first region (injection port) $23a'$ on micro-channel chip 10 to fill the interior of channel $22'$. Next, an analysis sample is injected. Furthermore, electrode rods $1a$ and $1b$ are inserted into second regions $24a'$ and $24b'$ to come into contact with carbon inks $16a$ and $16b$.

A voltage is applied to both ends of channel $22'$ by passing a current through electrode rods $1a$ and $1b$. This causes the sample to be electrophoresed through channel $22'$ toward through hole (exhaust port) $23b$.

Inside channel $22'$, the sample is separated according to the difference in the migration speed per molecular weight. A tester can obtain the electrophoresis result by detecting fluorescence intensity.

[Effect of Present Embodiment]

Figure 4:
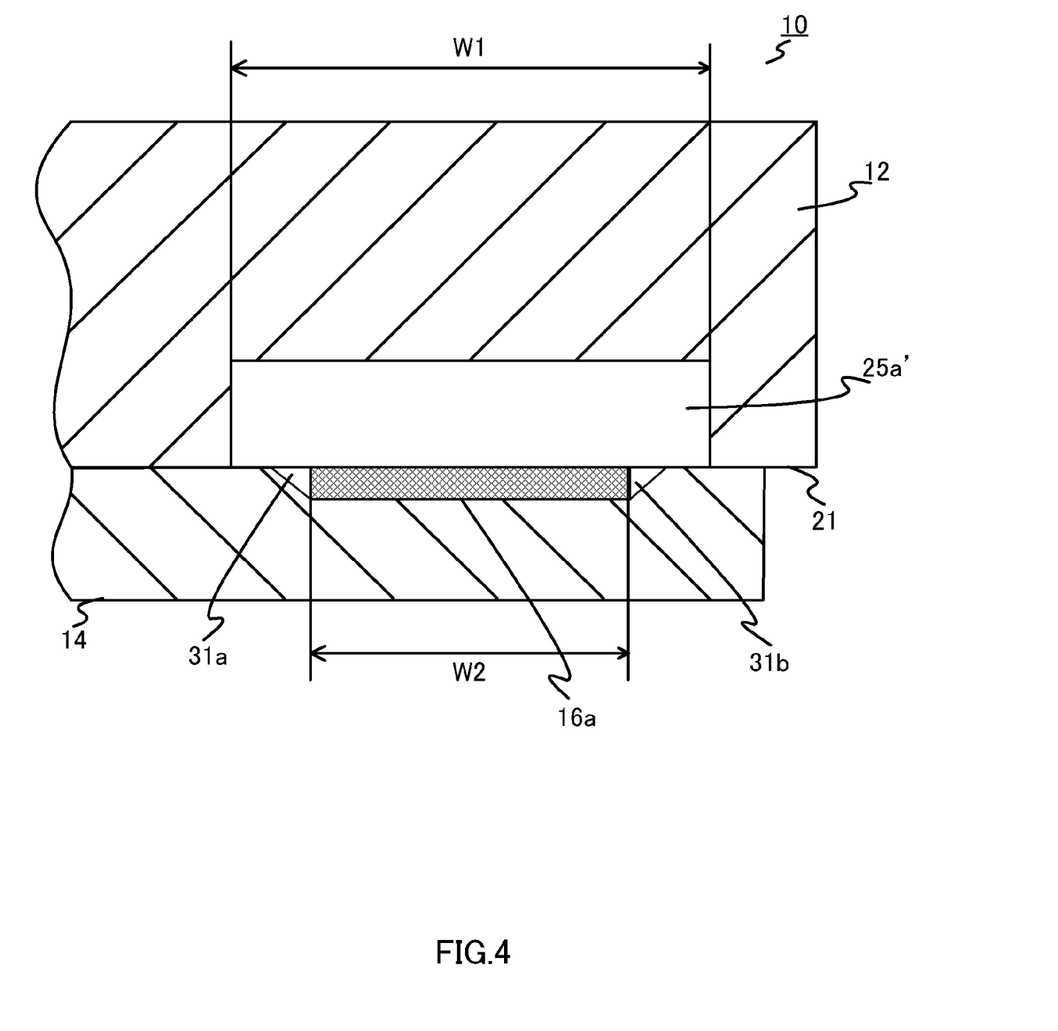
FIG. 4 is an enlarged cross-sectional view along line E-E of FIG. 1A.

FIG. 4 is an enlarged cross-sectional view along line E-E in FIG. 1A. As shown in FIG. 4, the peripheral portion of carbon ink $16a$ ($16b$) of film 14 remains unbonded (insufficiently laminated) to chip body 12 due to the thickness of carbon ink $16a$ ($16b$) and gaps $31a$ and $31b$ may be produced between chip body 12 and film 14 at edges of carbon ink $16a$ ($16b$).

Gaps $31a$ and $31b$ become unexpected channels and are connected to first region $23a'$ ($23b'$). Therefore, the liquid (buffer solution and, sample) injected into channel $22'$ of micro-channel chip 10 leaks along gaps $31a$ and $31b$ from first region $23a'$ ($23b'$).

Third region $25a'$ ($25b'$) is formed on micro-channel chip 10 according to the present embodiment. Width W1 of third region $25a'$ ($25b'$) is formed so as to be greater than width W2 of carbon ink $16a$ ($16b$). For this reason, third region $25a'$ ($25b'$) is connected to gaps $31a$ and $31b$.

Therefore, the liquid leaked along gaps $31a$ and $31b$ is stopped by or stored in third region $25a'$ ($25b'$) and does not go to second region $24a'$ ($24b'$).

As a result, according to the present embodiment, it is possible to prevent the liquid from leaking out and prevent contamination of the electrode or external environment.

[Variations]

Hereinafter, variations of the micro-channel chip according to the present embodiment will be described.

[Variation 1]

Figure 5A:
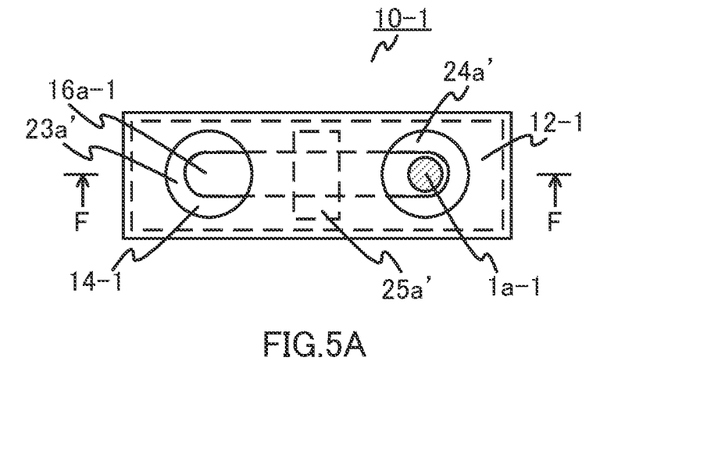
FIG. 5A to FIG. 5C are diagrams illustrating the shape of the micro-channel chip according to the embodiment of the present invention (variation 1)
Figure 5B:
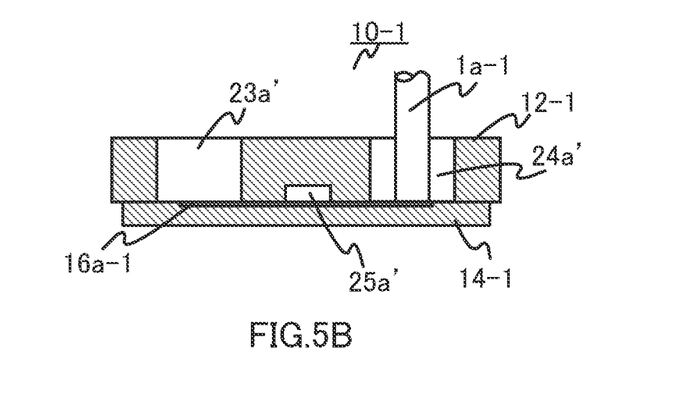
Figure 5C:
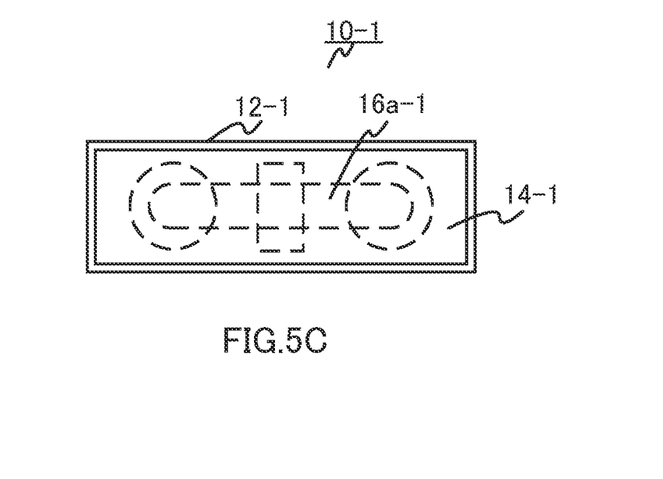

FIG. 5A to FIG. 5C are schematic views illustrating the shape of variation 1 of the micro-channel chip according to the present embodiment. The micro-channel chip of variation 1 is used to heat a sample using a heater. FIG. 5A is a plan view, FIG. 5B is a front cross-sectional view along line F-F and FIG. 5C is a bottom view. FIG. 5A and FIG. 5B show electric heater $1a$-1. In FIG. 5A to FIG. 5C, parts common to those in FIG. 1A to FIG. 1D are assigned the same reference numerals and detailed descriptions thereof will be omitted.

Figure 6A:
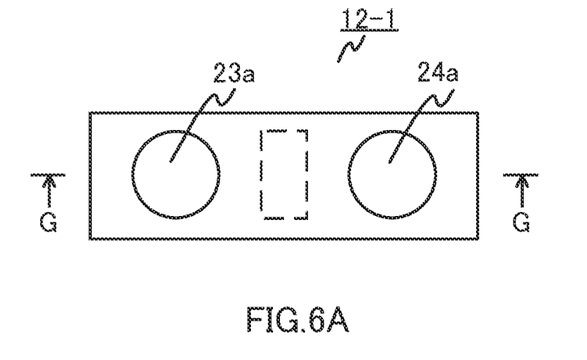
FIG. 6A to FIG. 6C are diagrams illustrating the shape of the chip body of the micro-channel chip shown in FIG. 5A to FIG. 5C.
Figure 6B:
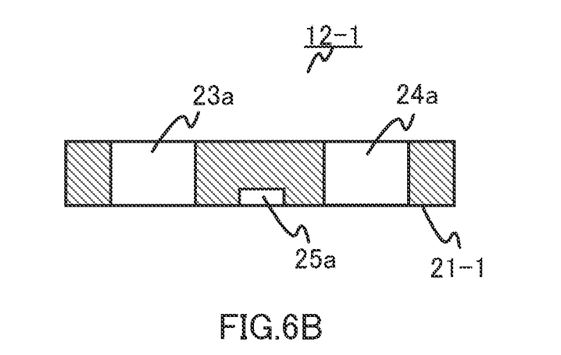
Figure 6C:
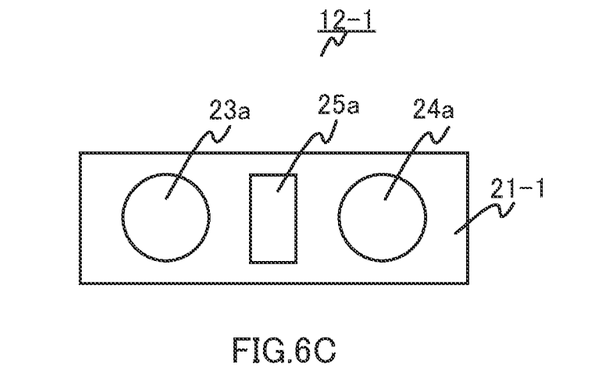

FIG. 6A to FIG. 6C are schematic views illustrating the shape of the chip body of the micro-channel chip in FIG. 5A to FIG. 5C. FIG. 6A is a plan view, FIG. 6B is a front cross-sectional view along line G-G and FIG. 6C is a bottom view. In FIG. 6A to FIG. 6C, parts common to those in FIG. 2A to FIG. 2D are assigned the same reference numerals and detailed descriptions thereof will be omitted.

Variation 1 is a case where there is only one metal film 16a-1 with an excellent heat transfer property as a transfer function section. In FIG. 5A to FIG. 5C, in micro-channel chip 10-1, the shapes of chip body 12-1 and film 14-1 are different from those of chip body 12 and film 14 in FIG. 1A to FIG. 1D.

Furthermore, in FIG. 6A to FIG. 6C, through hole 23a and through hole 24a are formed one each on chip body 12-1. Furthermore, one groove 25a is formed on undersurface 21-1 of chip body 12-1. No micro-groove is formed on chip body 12-1.

In variation 1, a liquid leaked out of first region 23a' is also stopped by or stored in third region 25a' and can thereby be prevented from reaching second region 24a'. As a result, it is possible to prevent this liquid from leaking, prevent contamination of an external environment and safely heat the sample injected into first region 23a' using electric heater 1a-1.

[Variation 2]

Figure 7A:
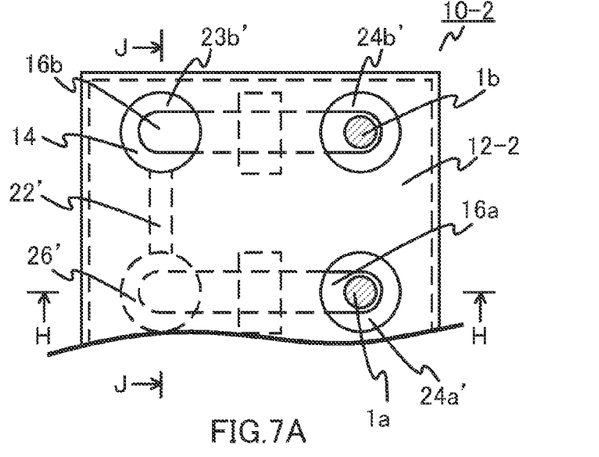
FIG. 7A to FIG. 7D are diagrams illustrating the shape of the micro-channel chip according to the embodiment of the present invention (variation 2)
Figure 7B:
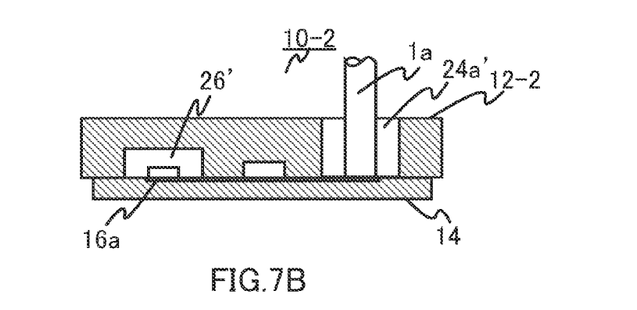
Figure 7C:
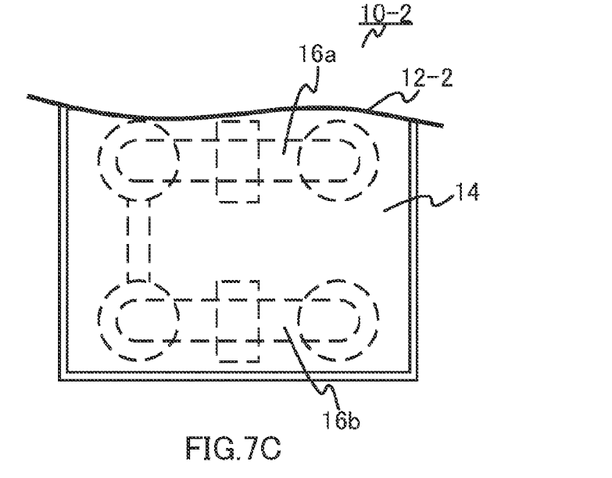
Figure 7D:
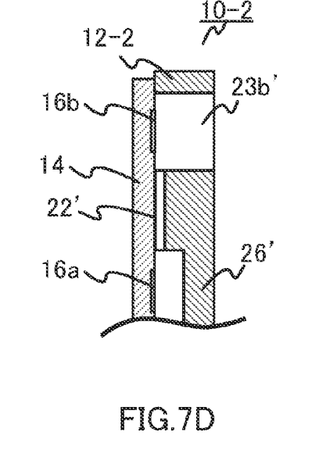

FIG. 7A to FIG. 7D are schematic views illustrating the shape of variation 2 of the micro-channel chip according to the present embodiment. In variation 2, part of the micro-channel chip for which the present invention is implemented will be shown and the configuration of the present invention will be described. FIG. 7A is a plan view, FIG. 7B is a front cross-sectional view along line H-H, FIG. 7C is a bottom view and FIG. 7D is a left side cross-sectional view along line J-J. FIG. 7A and FIG. 7B show electrode rods 1a and 1b together. In FIG. 7A to FIG. 7D, parts common to those in FIG. 1A to FIG. 1D are assigned the same reference numerals and detailed descriptions thereof will be omitted.

Figure 8A:
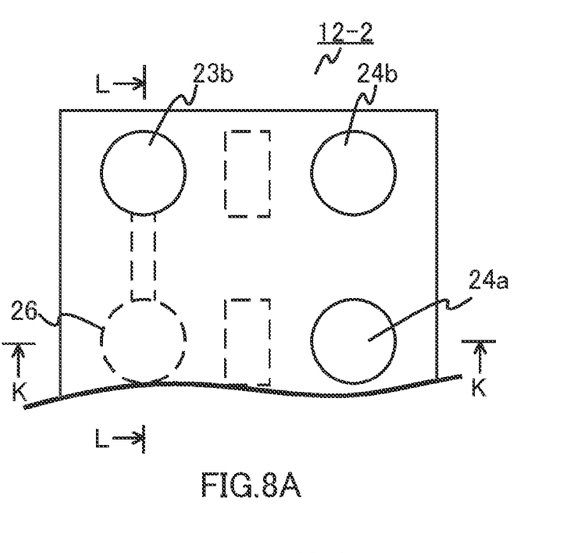
FIG. 8A to FIG. 8D are diagrams illustrating part of the shape of the chip body of the micro-channel chip shown in FIG. 7A to FIG. 7D.
Figure 8B:
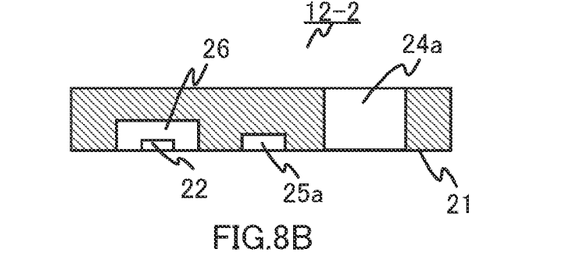
Figure 8C:
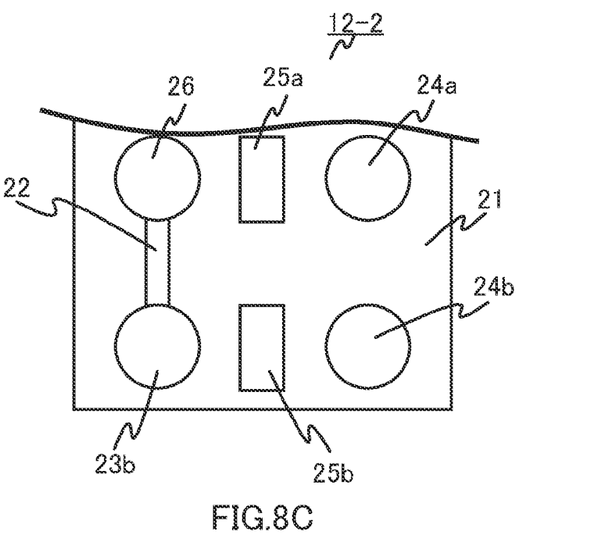
Figure 8D:
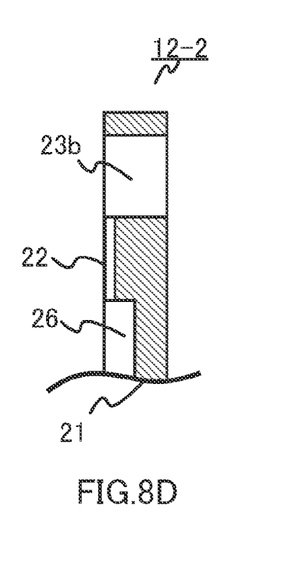

FIG. 8A to FIG. 8D are schematic views illustrating part of the shape of the chip body of the micro-channel chip in FIG. 7A to FIG. 7D. FIG. 8A is a plan view, FIG. 8B is a front cross-sectional view along line K-K, FIG. 8C is a bottom view and FIG. 8D is a left side cross-sectional view along L-L. In FIG. 8A to FIG. 8D, parts common to those in FIG. 2A to FIG. 2D are assigned the same reference numerals and detailed descriptions thereof will be omitted.

Variation 2 is a case where depression 26 is formed instead of through hole 23a. In FIG. 7A to FIG. 7D, in micro-channel chip 10-2, the shape of chip body 12-2 is different from that of chip body 12 in FIG. 1A to FIG. 1D.

Furthermore, in FIG. 8A to FIG. 8D, depression 26 is formed instead of through hole 23a on chip body 12-2. When chip body 12-2 and film 14 are bonded together, first region 26' is formed by closing the opening on the film 14 side of depression 26. In variation 2, the sample injected into first region 23b' moves along channel 22' and is stored in first region 26'.

In variation 2, the liquid leaked from first regions 26' and 23b' is also stopped by or stored in third regions 25a' and 25b', and so does not go to through holes 24a and 24b. As a result, it is possible to prevent the liquid from leaking and prevent contamination of the electrode or external environment.

[Variation 3]

Figure 9A:
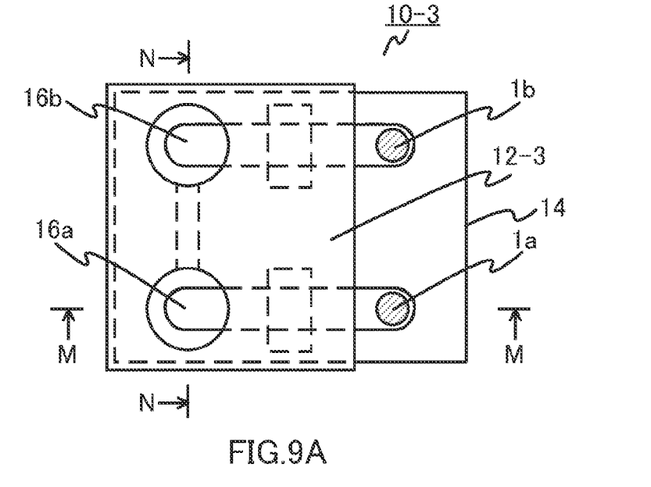
FIG. 9A to FIG. 9D are diagrams illustrating part of the shape of the micro-channel chip according to the embodiment of the present invention (variation 3)
Figure 9B:
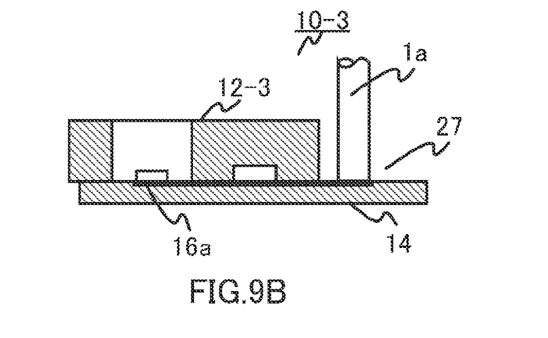
Figure 9C:
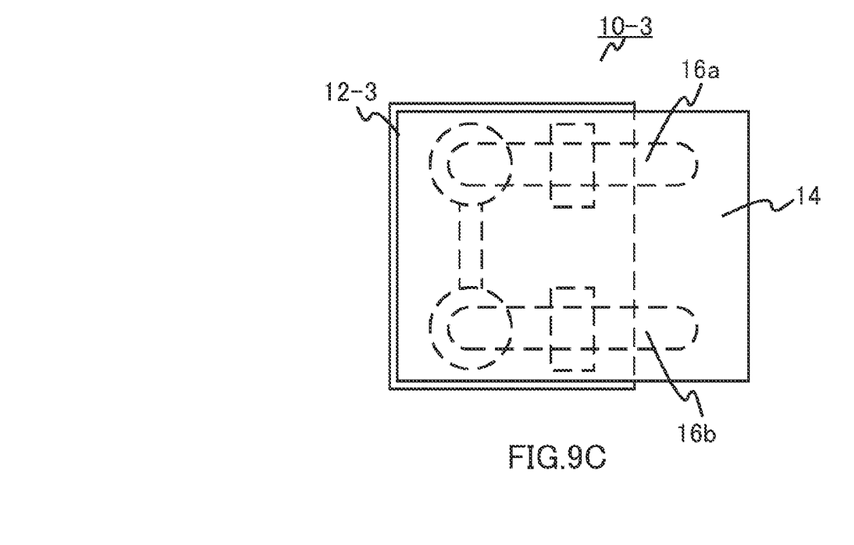
Figure 9D:
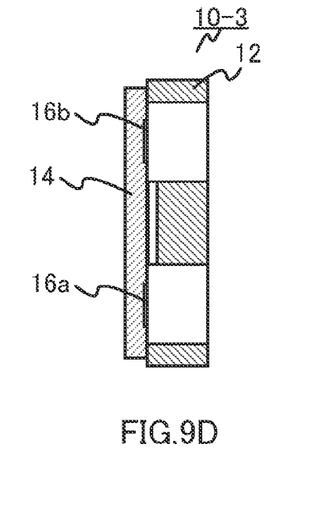

FIG. 9A to FIG. 9D are schematic views illustrating the shape of variation 3 of the micro-channel chip according to the present embodiment. FIG. 9A is a plan view, FIG. 9B is a front cross-sectional view along line M-M, FIG. 9C is a bottom view and FIG. 9D is a left side cross-sectional view along line N-N. FIG. 9A and FIG. 9B show electrode rods 1a and 1b together. In FIG. 9A to FIG. 9D, parts common to those in FIG. 1A to FIG. 1D are assigned the same reference numerals and detailed descriptions thereof will be omitted.

Figure 10A:
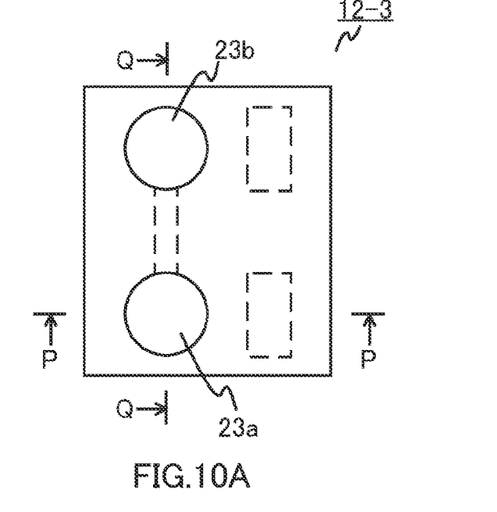
FIG. 10A to FIG. 10D are diagrams illustrating part of the shape of the chip body of the micro-channel chip shown in FIG. 9A to FIG. 9D.
Figure 10B:
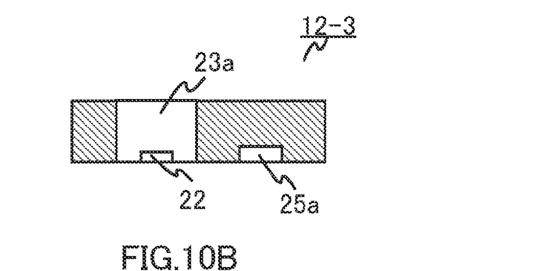
Figure 10C:
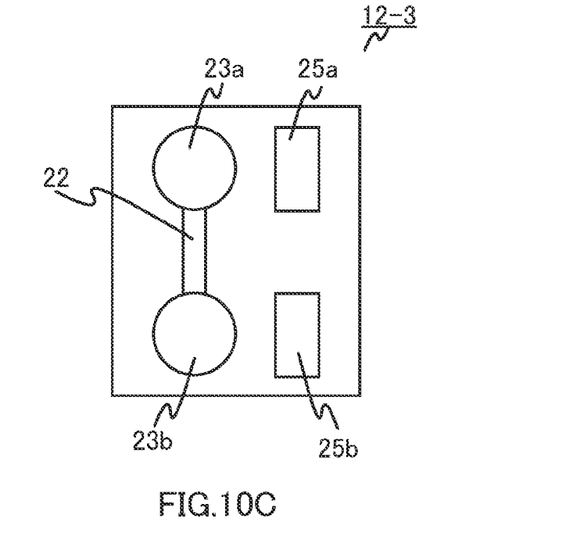
Figure 10D:
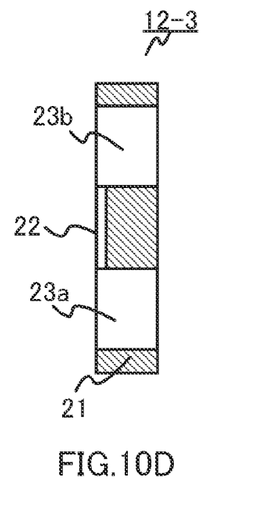

FIG. 10A to FIG. 10D are schematic views illustrating the shape of the chip body of the micro-channel chip in FIG. 9A to FIG. 9D. FIG. 10A is a plan view, FIG. 10B is a front cross-sectional view along line P-P, FIG. 10C is a bottom view and FIG. 10D is a left side cross-sectional view along line Q-Q. In FIG. 10A to FIG. 10D, parts common to those in FIG. 2A to FIG. 2D are assigned the same reference numerals and detailed descriptions thereof will be omitted.

Variation 3 is a case where through holes 24a and 24b are not formed and second region 27 is formed using chip body 12-3 which is smaller than film 14 so that ends of carbon inks 16a and 16b for contacting electrode rods 1a and 1b are exposed. As shown in FIG. 9A to FIG. 9D and FIG. 10A to FIG. 10D, the shape of chip body 12-3 is different from that of chip body 12 in FIG. 1A to FIG. 1D.

In variation 3, the liquid leaked from first regions 23a' and 23b' is stopped by or stored in third regions 25a' and 25b', and so does not go to second region 27. As a result, it is possible to prevent the liquid from leaking and prevent contamination of the electrode and external environment.

A case has been described in the above embodiment where carbon inks 16a and 16b are used as conductive members and metal film 16a-1 is used as a heat transfer member, but the present invention is not limited to this, and similar effects can be obtained even when other conductive members or heat transfer members are used.

A case has been described in the above embodiment where carbon inks 16a and 16b are printed, but the present invention is not limited to this, and similar effects can also be obtained using other methods such as pasting or vapor depositing a conductive member or heat transfer member.

A case has been described in the above embodiment where film 14 is bonded to chip body 12, but the present invention is not limited to this, and similar effects can be obtained even when a thin plate is bonded to a chip body as disclosed Patent Reference.

Furthermore, a case has been described in the above embodiment where through holes 24a and 24b are formed to insert electrode rods 1a and 1b, and electric heater 1a-1, but the present invention is not limited to this, and similar effects can also be obtained for a micro-channel chip in a mode in which one end of a conductive member (heat transfer member) is exposed outside the chip body as disclosed in Patent Reference.

As shown in the above embodiment, the present invention forms a space (third region) communicating with gaps (unexpected channels) that can be produced at edges of a transfer function section between a space (first region) into which a liquid is introduced and a space (second region) electrically or thermally connected thereto via the transfer function section, and thereby prevents the liquid introduced into the first region from leaking out to the space of the second region. The shape of the substrate member for forming the first region and the second region is not limited to the shape shown in the above embodiment as long as this effect can be obtained.

The fluid handling apparatus and the fluid handling system according to the present invention can be used for an apparatus that carries out an inspection/analysis of trace substances accurately and at high speed in the scientific field such as biochemistry and analytical chemistry or medical field.

The invention claimed is:

1. A fluid handling apparatus comprising:
a substrate member;
a cover member joined to one surface of the substrate member; and
a transfer function section formed on the cover member for transferring electricity or heat, said transfer function section being formed in a laminar shape so as to cover a part of a surface of the cover member, wherein
said substrate member includes a depression or a through hole constituting a first region formed in the one surface thereof at a portion corresponding to one end of the transfer function section,
said cover member is disposed to close an opening of the depression or the through hole,
said transfer function section includes the other end corresponding to a second region communicating with an outside,
said transfer function section is disposed to electrically or thermally connect the first region and the second region,
said substrate member further includes a groove constituting a third region formed in the one surface thereof so as to extend over an edge of the transfer function section extending between the first region and the second region,
said cover member is disposed to cover an opening of the groove, and
said transfer function section is exposed to the first region, the second region and the third region.

2. A fluid handling system comprising the fluid handling apparatus according to claim 1.

* * * * *